United States Patent
Matsutani et al.

(10) Patent No.: US 10,575,845 B2
(45) Date of Patent: Mar. 3, 2020

(54) SUTURE NEEDLE

(71) Applicant: Mani, Inc., Tochigi (JP)

(72) Inventors: Masaaki Matsutani, Tochigi (JP); Shinichi Akutsu, Tochigi (JP); Masato Mizui, Tochigi (JP); Takashi Ishida, Tochigi (JP)

(73) Assignee: MANI, INC., Tochigi (JP)

( * ) Notice: Subject to any disclaimer, the term of this patent is extended or adjusted under 35 U.S.C. 154(b) by 317 days.

(21) Appl. No.: 15/506,845

(22) PCT Filed: Aug. 26, 2015

(86) PCT No.: PCT/JP2015/074040
§ 371 (c)(1),
(2) Date: Feb. 27, 2017

(87) PCT Pub. No.: WO2016/031865
PCT Pub. Date: Mar. 3, 2016

(65) Prior Publication Data
US 2017/0252037 A1 Sep. 7, 2017

(30) Foreign Application Priority Data
Aug. 29, 2014 (JP) .................. 2014-174868

(51) Int. Cl.
*A61B 17/06* (2006.01)
(52) U.S. Cl.
CPC ............ *A61B 17/06066* (2013.01); *A61B 2017/06071* (2013.01)
(58) Field of Classification Search
CPC .......... A61B 17/06066; A61B 17/3211; A61B 2017/00526; A61B 2017/06071; A61B 2017/0608
See application file for complete search history.

(56) References Cited

U.S. PATENT DOCUMENTS

| 4,513,747 A | 4/1985 | Smith |
| 5,749,897 A | 5/1998 | Matsutani et al. |
| | (Continued) | |

FOREIGN PATENT DOCUMENTS

| JP | H03-70493 B2 | 11/1991 |
| JP | H04-94834 A | 3/1992 |
| | (Continued) | |

OTHER PUBLICATIONS

International Search Report for Application No. PCT/JP2015/074040 dated Dec. 1, 2015.

*Primary Examiner* — Robert A Lynch
(74) *Attorney, Agent, or Firm* — Isshiki international Law Office; Joseph P. Farrar, Esq.

(57) ABSTRACT

Strength of a front end part having a sharp point of a medical suture needle is maintained and resistance when piercing tissue is reduced. There is provided a medical suture needle having a triangular cross section made of austenitic stainless steel having a fibrously extending structure, having two first slanted surfaces (11) ground and sandwiching a ridge (20), and a bottom surface (13) sandwiched between the two first slanted surfaces and ground. The ridge is formed comprising a first cutting blade (1) that is formed by the two first slanted surfaces (11) intersecting, a ridge part (20) that is formed on a body part side of the first cutting blade without the first slanted surfaces (11) intersecting, and a second cutting blade (2) that is formed by two second slanted surfaces (12) ground, intersecting and sandwiching the first cutting blade (1) on a front end side of the first cutting blade (1). Length L2 of the first cutting blade is within a range of 3 to 20 times length L1 of the second cutting blade (2), and a front end (3) of the second cutting blade (2) is positioned deviating from the material center.

2 Claims, 2 Drawing Sheets

(56) References Cited

U.S. PATENT DOCUMENTS

| | | |
|---|---|---|
| 2003/0004527 A1 | 1/2003 | Matsutani et al. |
| 2004/0098048 A1* | 5/2004 | Cunningham ... A61B 17/06066 606/223 |
| 2011/0112575 A1 | 5/2011 | Tochimura et al. |
| 2012/0323264 A1 | 12/2012 | Matsutani |

FOREIGN PATENT DOCUMENTS

| | | |
|---|---|---|
| JP | 05-056983 A | 3/1993 |
| JP | H08-57566 A | 3/1996 |
| JP | H11-70113 A | 3/1999 |
| JP | 2002345834 A | 12/2002 |
| JP | 2009285455 A | 12/2009 |
| JP | 2011172786 A | 9/2011 |
| WO | 2016031865 A1 | 3/2016 |

* cited by examiner

SUTURE NEEDLE

CROSS-REFERENCE TO RELATED APPLICATIONS

The present application is a national phase entry under 35 U.S.C. § 371 of International Application No. PCT/PCT2015/074040, filed Aug. 26, 2015, which claims priority from Japanese Patent Application No. 2014-174868 filed Aug. 29, 2014, the entire disclosures of which are incorporated by reference herein.

TECHNICAL FIELD

The present invention relates to a medical suture needle having a triangular cross section used for suturing biomedical tissue. It particularly relates to a medical suture needle having low impalement resistance and high strength.

BACKGROUND ART

Multiple kinds of medical suture needles having optimum shapes corresponding to the target suture sections are provided. Among them is a medical suture needle called a triangular needle constituted by a blade part that has a sharp point and a cutting blade continuing from the point, wherein the blade part has a triangular cross section. A typical triangular needle is constituted by a blade part, which becomes thicker as it approaches a body part from the front end and has a cutting blade formed on at least one ridgeline, a body part which is formed continuing from the blade part and grasped using a needle holder, and a base end part which is formed continuing from the body part and to which a suture thread is attached.

A triangular needle described in Patent Document 1, for example, is formed in a triangular shape by press working or grinding an end of a material, and then it is further ground to form a cutting blade on an edge intersecting with the ground surface. A sharp point is then formed on the front end of the formed cutting blade. This triangular needle has three surfaces formed by grinding in approximately the same manner, and is constituted such that the angles making the respective cutting blades on the front end part are within a range of 25 to 30 degrees. This angle allows suturing by passing the needle through a target tissue without deforming the point when piercing the tissue.

Moreover, a triangular needle described in Patent Document 2 has a main body part that has two nearly parallel surfaces, wherein a first flat surface, which results from grinding a surface (bottom) constituting the main body part, is made to intersect with a second flat surface so as to form a first incision blade and then gathered together facing a third flat surface made up of the other surface (top). Formation of a fourth and a fifth flat surface on the front end of the first incision blade then forms a fourth incision blade continuing from the first incision blade. More specifically, it is configured such that the third flat surface is nearly parallel to the axis of the needle. As a result, the third flat surface remains as a pressing surface of the main body part, and a front end of the fourth incision blade coincides with the third flat surface.

With the triangular needle described in Patent Document 2, an angle made by a fifth incision blade and a sixth incision blade in the third flat surface is preferably 30 to 45 degrees, and angle made by a second incision blade and a third incision blade in the third flat surface is preferably 12 to 15 degrees. Moreover, an angle made by the third flat surface and the fourth incision blade is preferably 30 to 37 degrees, and angle made by the third flat surface and the first incision blade is preferably 11 to 13 degrees.

PRIOR ART DOCUMENTS

Patent Documents

[Patent Document 1] JP H05-056983A
[Patent Document 2] JP H03-070493A

SUMMARY

Problem to be Solved

Triangular needle having cutting blades as described in Patent Documents 1 and 2 pierces the tissue with a sharp point and incises the tissue by cutting blades, and passes a body part and a base end part through this incised portion in order to pass a suture thread through. As a result, resistance when piercing the tissue with the point and resistance when incising the tissue are burdens to the doctor, and reducing these burdens has become a big challenge of development.

Particularly in the case of a triangular needle, there is a problem that while the resistance when passing through the tissue can be reduced if the increasing rate of thickness of the blade part is low, the sharp point formed on the front end is easily deformed when pierced through the tissue.

An object of the present invention is to provide a medical suture needle capable of improving strength of a front end part where a sharp point is formed and reducing resistance when piercing through tissue.

Solution to the Problem

A medical suture needle according to the present invention for resolving the above problem is characterized by having a triangular cross section made of austenitic stainless steel having a fibrously extending structure, having two first slanted surfaces ground and sandwiching a ridge, and a bottom surface sandwiched between the two first slanted surfaces and ground. The ridge is formed comprising a first cutting blade that is formed by the two first slanted surfaces intersecting, a ridge part that is formed on a body part side of the first cutting blade without the two first slanted surfaces intersecting, and a second cutting blade that is formed by two second slanted surfaces ground, intersecting and sandwiching the first cutting blade on a front end side of the first cutting blade. Length of the first cutting blade is within a range of 3 to 20 times length of the second cutting blade, and a front end of the second cutting blade is positioned deviating from the material center.

It is preferable that the above medical suture needle has an angle made by cut upper rims having as a starting point an end part of the first cutting blade on the two slanted surfaces that are ground and sandwiching the ridge is smaller than 20 degrees.

Moreover, it is preferable that either of the above medical suture needles has grind marks of the first slanted surfaces formed along the length of the medical suture needle, and grind marks of the second slanted surfaces and the bottom surface formed crossing the length of the medical suture needle.

Advantageous Effects

With the medical suture needle according to the present invention, a first cutting blade having two first slanted surfaces intersecting is formed in the ridge, a second cutting blade having two second slanted surfaces intersecting is formed on a front end side of the first cutting blade, length of the first cutting blade is within a range of 3 to 20 times length of the second cutting blade, and a front end of the first cutting blade is positioned deviating from the material center.

Therefore, when comparing slant of the first cutting blade and slant of the second cutting blade, the slant of the second cutting blade is greater. Accordingly, an increasing rate of thickness of the part in which the first cutting blade is formed may be reduced so as to reduce the resistance when incising the tissue. Moreover, the increasing rate of thickness of the part in which the second cutting blade is formed may be increased so that the front end part does not deform easily.

Setting the length of the first cutting blade according to the proportion to the second cutting blade and not according to an angle allows changing of the increasing rate of thickness in accordance with the diameter of the material of the medical suture needle, and having an optimum resistance for incision. That is, while the length of the cutting blade is increased in accordance with the diameter of the material when the angle of the cutting blade portion is constant, the length of the cutting blade may be optimum regardless of the diameter of the material when the angle of the cutting blade is set according to the proportion of the first cutting blade to the second cutting blade.

Furthermore, since the second cutting blade has two intersecting second slanted surfaces that are formed intersecting on the front end of the first cutting blade, the front end portion of the second cutting blade is positioned slightly closer to the center of the material from the first cutting blade. Therefore, the point corresponds to the region having the highest hardness of austenitic stainless steel having a fibrously extending structure, the resistance when piercing through tissue may be reduced, and fear of deformation may also be reduced.

Yet further, the length of the first cutting blade may be regulated by making the angle made by cut upper rims of the two first slanted surfaces having the end part of the first cutting blade in the ridge as a starting point be smaller than 20 degrees.

Yet even further, resistance when the point pierces through the tissue may be reduced by forming grind marks of the first slanted surfaces along the length of the needle and forming grind marks of the second cutting blade crossing the length of the needle.

DESCRIPTION OF EMBODIMENTS

A medical suture needle according to the present invention is described below. The medical suture needle according to the present invention is constituted by a wire rod material made of austenitic stainless steel having a fibrously extending structure. That is, by subjecting the wire rod made of austenitic stainless steel to cold drawing processing at a predetermined area reduction rate, the needle is formed having the thickness of the medical suture needle to be used, using a fibrously extending wire rod as a material.

The material subjected to cold drawing processing at a predetermined area reduction rate may display high hardness through work hardening. Particularly, since this kind of material does not display uniform hardness across the entire cross section, it has a characteristic in a layer formed having the highest hardness slightly on the inner side rather than the outer surface.

With the present invention, the medical suture needle to be used is formed in a triangular shape (referred to as 'triangular needle' hereafter), and cutting blades (a first cutting blade and a second cutting blade) are formed on the front end side of ridges. Since the length of the first cutting blade is within a range of 3 to 20 times the length of the second cutting blade, the increasing rate of thickness of the part in which the first cutting blade is formed is lower than increasing rate of thickness of the part in which the second cutting blade is formed. As a result, the second cutting blade is not easily deformed when piercing tissue even if there is resistance from the tissue, and once the second cutting blade has pierced the tissue, resistance when incising the tissue by the first cutting blade is reduced.

If the length of the first cutting blade becomes three times smaller than that of the second cutting blade, the increasing rate of thickness of the part in which the first cutting blade is formed is extremely large, and the resistance when incising the tissue increases, possibly increasing fatigue of the doctor, and is thus not preferred. Moreover, if the length of the first cutting blade becomes 20 times larger than that of the second cutting blade, it is easily bent when incising the tissue, there is fear that stable suturing cannot be performed, and is thus not preferred.

Note that in the description below, 'thickness' does not refer to the diameter of a circle connecting the vertices of the triangle nor the diameter of the inscribed circle of the three sides, but refers to the diameter of a circle having an area corresponding to the area of the triangle. Moreover, 'ridge' includes a part having an incising function comprised by the first cutting blade and the second cutting blade, and a ridge part not having an incising function.

Figure 1:
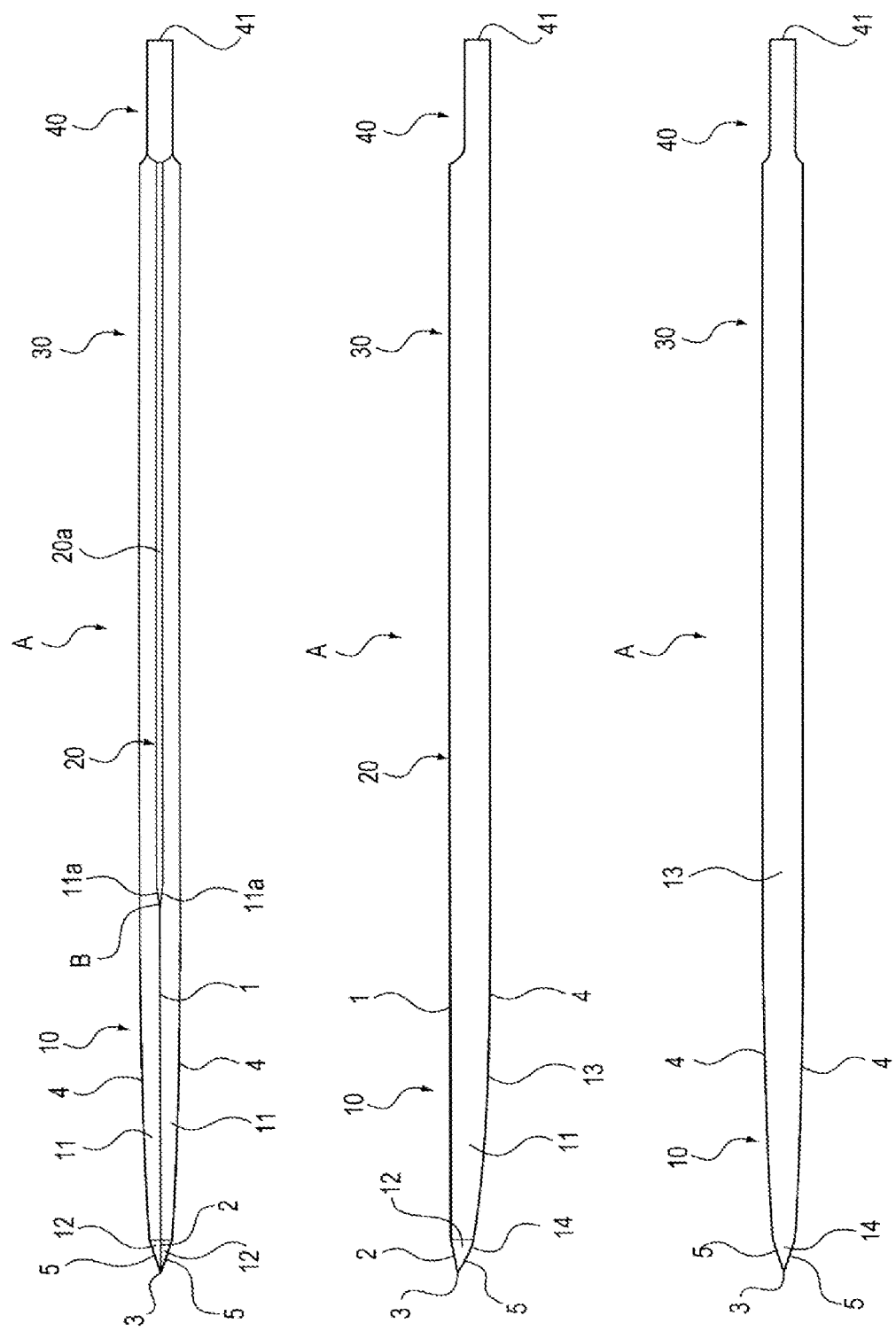
FIG. 1 is a diagram for describing an overall structure of a medical suture needle according to an embodiment.
Figure 2:
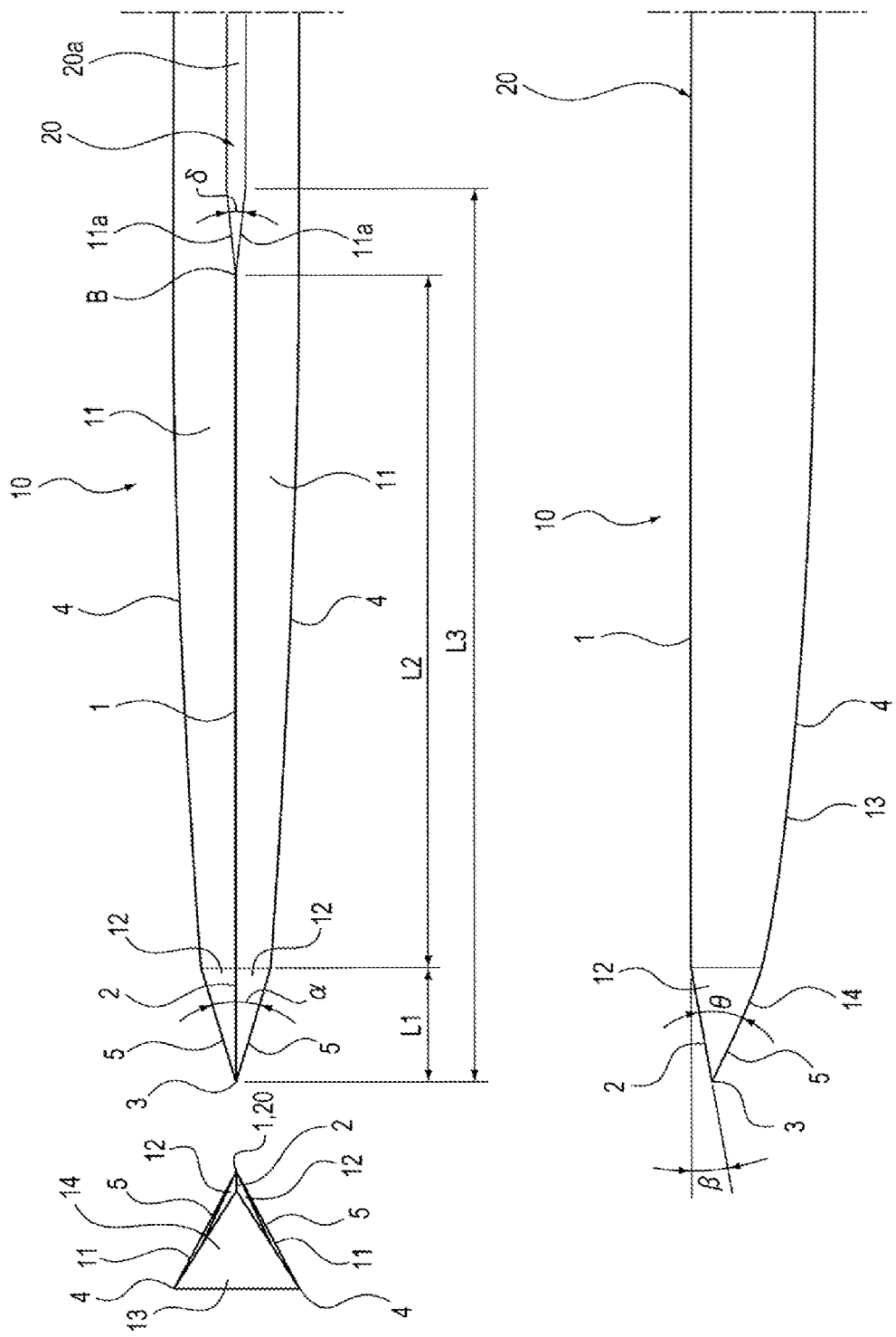
FIG. 2 shows magnified views for describing principal parts of the medical suture needle according to the embodiment.

A configuration of a triangular needle according to an embodiment is described below. A triangular needle A illustrated in FIG. 1 is formed in a straight form, and it may be used as a suture needle as is, or the straight triangular needle A may be bent in a later step and used as a curved suture needle. Note that while the boundaries of first slanted surfaces 11 and second slanted surfaces 12 are indicated by solid lines in FIG. 1 and FIG. 2, the solid lines are given to facilitate description, and in an actual suture needle, they are so smoothly connected that it is difficult to discern the boundaries.

The triangular needle A according to the embodiment is formed by cutting to a predetermined length, a wire rod made of austenitic stainless steel that has been subjected to cold drawing processing until a predetermined diameter D, subjecting the end side to press working into a triangular prism, grinding the triangular prism, and making a blind hole in the resulting triangular prism.

The triangular needle A has a cutting blade part 10 formed on one side, a body part 30 for a doctor to grasp using a needle holder so as to maneuver is formed continuing to the cutting blade part 10, and a base end part 40 for attaching a suture thread omitted from the drawing is formed continuing to the body part 30. The triangular needle A, has the cutting blade part 10 and the body part 30 formed having a triangular cross section. Moreover, as described later, a ridgeline corresponding to the apex of the triangle is a ridge 20 that includes the first cutting blade 1, the second cutting blade 2, and a ridge part 20*a*, surfaces corresponding to two slanted sides become the first slanted surface 11 and the second slanted surface 12, and surfaces corresponding to bases become a first bottom surface 13 and a second bottom surface 14.

The triangular needle A according to the embodiment has the base end part 40 formed having a circular cross section, and a blind hole omitted from the drawing formed in an end surface 41. An end of the suture thread is then inserted through the blind hole and attached by caulking the part corresponding to the blind hole in the base end part 40. However, the structure for attaching the suture thread to the triangular needle is not limited to only the embodiment, and may naturally have a structure where the base end part 40 is formed in a flat shape, a pair of springy posts is formed on the formed flat surface, and the suture thread is passed through between the posts and then attached.

The cutting blade part 10 has a function of piercing and incising tissue to be sutured. This cutting blade part 10 has a sharp point 3 formed on the front end, and between the point 3 and the body part 30, the first cutting blade 1 is formed on the body part 30 side and the second cutting blade 2 is formed on the point 3 side.

The two first slanted surfaces 11 from the cutting blade part 10 to the body part 30 sandwiching the ridge 20 that is formed along the length of the triangular needle A are ground. The two first slanted surfaces 11 are formed by being ground along the length of the triangular needle A, leaving grind marks formed along the length of the first slanted surfaces 11 as a result.

The two first slanted surfaces 11 approach each other toward the point 3 side and intersect each other at the part corresponding to the ridge 20, thereby forming an edge, which is formed as the first cutting blade 1. In addition, a range (range of L1+L2 illustrated in the top view of FIG. 2) within which the second cutting blade 2 and the first cutting blade 1 are formed from the point 3 is the cutting blade part 10.

Moreover, the two first slanted surfaces 11 made from the ground surfaces separate from each other on the body part 30 side and break away from the surface of the material. As a result, a ridge part 20*a* that does not have a function as a cutting blade is formed on the body part 30. Therefore, a base point B, which becomes a starting point of the first cutting blade 1 where the two first slanted surfaces 11 begin to intersect each other, and becomes a starting point of the ridge part 20*a* that does not have a function as a cutting blade, is formed at the ridge 20.

At the ridge 20 on the body part 30 side from the base point B, the two first slanted surfaces 11 break away without intersecting each other, thereby forming the ridge part 20*a* that does not have a function as a cutting blade between the two first slanted surfaces 11. Therefore, cut upper rims 11*a* of the two first slanted surfaces are formed in the ridge part 20*a* having the base point B as a starting point. That is, the boundaries between the ridge part 20*a* and each of the first slanted surfaces 11 are the cut upper rims 11*a*, respectively. An angle δ made by the two cut upper rims 11*a* having the base point B as a starting point is smaller than 20 degrees.

When the angle δ of the two cut upper rims 11*a* having the base point B as a starting point is 20 degrees or larger, the increasing rate of thickness along the first slanted surfaces 11 is extremely larger on the body part 30 side than on the base point B side, and incision resistance increases, which is not preferred. Moreover, the ridge 20 becomes more like an edge as the angle δ approaches zero, and thus there is fear that it may function as a cutting blade however inadequate it may be. Therefore, the angle δ made by the two cut upper rims 11*a* having the base point B as a starting point is preferably less than 20 degrees, more preferably within a range of 5 to 10 degrees.

The first cutting blade 1 is formed extending from the base point B of the ridge 20 toward the point 3 side, and is formed in a linear form parallel to the ridge 20 either coinciding with the ridge 20 in accordance with the ground depth of the first slanted surfaces 11, or shifting slightly to the center side from the ridge 20.

Two ground, second slanted surfaces 12, which sandwich the first cutting blade 1, intersect on the front end side of the first cutting blade 1, and an edge is formed, as the second cutting blade 2, by the two intersecting second slanted surfaces 12. The two second slanted surfaces 12 approach each other toward the front end and make contact with each other, thereby forming the point 3.

A part corresponding to the second cutting blade 2 is first so formed that the part faces downward toward the center with an angle β corresponding to the first cutting blade 1 falling within a range of 7 to 10 degrees (8 degrees in the embodiment), and the second cutting blade is then formed in this downward-facing, slanted part. The second cutting blade 2 is formed by grinding the downward-facing slanted part in a direction crossing the length of the triangular needle A. Accordingly, the second cutting blade 2 is formed within the range of the angle β to the first cutting blade 1, and has the grind marks crossing the length thereof.

The point 3 is at the front end of the second cutting blade 2, and is formed there at which the two second slanted surfaces 12 and a second bottom surface 14 described later converge. Therefore, the point 3 is positioned on the center side from the circumference surface of the material made of austenitic stainless steel having a fibrously extending structure, and may have high hardness.

The first bottom surface 13 is formed on the opposite side to the ridge 20. This first bottom surface 13 is sandwiched between the two first slanted surfaces 11, and the first bottom surface 13 and the two first slanted surfaces 11 intersect and form edges 4, respectively. The edges 4 may or may not have a function as cutting blades.

A second bottom surface 14 is formed on the front end side of the first bottom surface 13 and corresponding to the second cutting blade 2. The second bottom surface 14 and the second slanted surfaces 12 intersect and form edges 5, respectively. As with the aforementioned edges 4, these edges 5 may or may not have a function as cutting blades.

Above, the first bottom surface 13 and the second bottom surface 14 are formed as continuous surfaces, and are formed slanted so that they approach the first cutting blade 1 and the second cutting blade 2. Therefore, when forming the first bottom surface 13 and the second bottom surface 14, a grinding member having a continuous form made from the two bottom surfaces is used, and the surfaces are ground in a direction crossing the length of the triangular needle A using the grinding member.

An angle made by the edges 5 having the point 3 of the second cutting blade 2. as a starting point (an angle α in the top view of FIG. 2) is set in the same manner as for triangular needles provided in the past (e.g., the triangular needle described in Patent Document 1.) For example, in the embodiment, the angle α is set within a range of 27 to 37 degrees.

Moreover, in the embodiment, an angle θ made by the second cutting blade 2 and the second bottom surface 14 is set within a range of 25 to 30 degrees. The range of this angle θ is approximately the same range as with the conventional triangular needle; however, since the second cutting blade 2 is slanted downward more than the first cutting blade 1 in the embodiment, setting the angle θ while taking the angle β into account is favorable.

Furthermore, length of the second cutting blade 2 (L1 in the top view of FIG. 2) is set so that it does not vary significantly even when the diameter D of the material for forming the triangular needle A to be used is changed. Namely, L1 is set to approximately 1D when the diameter D of the material is small, and L1 is set to approximately 0.4D when the diameter D of the material is large. Accordingly, the projected length L1 of the second cutting blade 2 is set within a range of approximately 0.4D to 1.0D.

On the other hand, length of the first cutting blade 1 (L2 in the top view of FIG. 2) is set within a range of 3 to 20 times the length of the second cutting blade 2. Namely, the length L2 of the first cutting blade is not set in accordance with the angle made by the two edges 4, but is set in accordance with the length L1 of the second cutting blade 2. Particularly, in the embodiment, the length L2 of the first cutting blade 1 is set so that the relationship with the diameter D of the material of the triangular needle A to be used is within a range of 5D to 6.6D while maintaining the aforementioned relationship with the length of the second cutting blade 2.

In the embodiment, length until the ridge part 20a where the two first slanted surfaces 11 break away from the slanted surfaces of the triangular needle A (L3 in the top view of FIG. 2) is set so that the relationship with the diameter D of the material of the triangular needle A to be used is within a range of 8.5D to 10D.

The process of manufacturing the triangular needle A configured as described above is briefly described. First, development of the triangular needle A to be used is determined, the diameter D of the material is established, and the relationship between the lengths of the first cutting blade 1 and the second cutting blade 2 is also established. Namely, size specifications of the triangular needle A are established.

Based on the established specifications, a wire rod made of austenitic stainless steel having a fibrously extending structure and a diameter corresponding to the thickness of the triangular needle A to be used is selected. This wire rod is cut to a length corresponding to the length of the triangular needle A to be used so as to form the material. A base end part 40 is prepared by making a blind hole in an end surface 41 on an end side of the material.

A triangular prism is shaped by press working an end side while grasping the base end part 40, and parts corresponding to the cutting blade part 10 and the body part 30 are formed. Through this shaping are formed a ridgeline corresponding to the ridge 20, slanted sides corresponding to the two first slanted surfaces, and a base corresponding to the first bottom surface 13.

Next, grinding along the length of the material while grasping the base end part 40 side of the material forms the two first slanted surfaces 11 and the first cutting blade 1 on which the first slanted surfaces 11 intersect. The two first slanted surfaces 11 approaching each other on the front end side of the material due to this grinding makes the first slanted surfaces 11 break away from the material on the body part 30, forming the base point B of the ridge 20 as a result. In addition, the cut upper rims 11a of the first slanted surfaces 11 are formed from the base point B, respectively, and the ridge part 20a is formed on the body part 30 side of the first cutting blade 1 from the base point B.

In the case of grinding the two first slanted surfaces 11 as described above, the grinding length is not set by an angle but by pre-established relationships with the length L1 of the second cutting blade 2 and with the diameter D of the material, wherein a range of length with allowance for a margin for grinding the front end part off when forming the second cutting blade 2 at the preset length L2 is ground. More specifically, when the length L2 of the first cutting blade 1 is set to 6D in accordance with the length L1 of the second cutting blade 2, it is preferable to set the length when grinding the two first slanted surfaces 11 to approximately 6.5D to 7.0D.

Next, the front end of the first cutting blade 1 formed as described above is ground so as to form the second cutting blade 2. That is, the front end sides of the two first slanted surfaces 11, which constitute the first cutting blade 1, are ground in a direction crossing the length of the triangular needle A so as to form the second slanted surfaces 12, respectively, and form the second cutting blade 2 having the second slanted surfaces 12 intersecting with each other.

When grinding the two second slanted surfaces 12, the material ground to make the first slanted surfaces 11 is made to slant at half of the angle θ from the abrasive grain surface of the grinding member and also to slant at the angle β from an extended line of the first cutting blade 1, and is then ground in the same state to the preset length L1 in accordance with the diameter D of the material of the second cutting blade 2.

Formation of the first slanted surfaces 11 and the second slanted surfaces 12 by grinding as described above forms the first cutting blade 1 and the second cutting blade 2. However, the sharp point 3 is not formed on the front end of the second cutting blade 2.

Next, the first bottom surface 13 and the second bottom surface 14 that are opposite to the first cutting blade 1 and the second cutting blade 2 each are ground in a direction crossing the length of the material. This grinding of the material is carried out by grinding the bottom surface parallel to the first cutting blade 1 in a slanted, upward, smooth curve toward the front end of the second cutting blade 2. The boundary between the first bottom surface 13 and the second bottom surface 14 is particularly connected by a smooth surface. Formation of the first bottom surface 13 makes the first bottom surface 13 and the first slanted surfaces 11 intersect, thereby forming edges 4, and formation of the second bottom surface 14 makes the second bottom surface 14 and the second slanted surfaces 12 intersect, thereby forming edges 5.

Moreover, the second cutting blade 2, the two second slanted surfaces 12, and the second bottom surface 14 converge, forming the point 3.

Note that the order of forming the two second slanted surfaces 12 and the second bottom surface 14 is not always after the second cutting blade 2 is formed as described above, but the first bottom surface 13 and the second bottom surface 14 may be ground before grinding the two second slanted surfaces 12 that constitute the second cutting blade 2. That is, even a method of forming the first bottom surface 13 and the second bottom surface 14 after the two first slanted surfaces 11 are ground to form the first cutting blade 1, and then grinding the second slanted surfaces 12 to form the second cutting blade 2 at the end allows formation of the suture needle A to be used.

Afterward, an electrolytic polishing process and a silicone coating process are carried out so as to manufacture the triangular needle A to be used. Note that when the triangular needle to be used is a curved needle, bending is carried out before the electrolytic polishing process.

Comparison of cutting quality of the triangular needle A according to the present invention and a conventional triangular needle having a cutting blade angle of approximately 30 degrees is explained next. In comparative tests, ten samples of the triangular needle A and the same of the conventional triangular needle with the same diameter D are fabricated, and each of the samples is impaled through the same synthetic resin sheet ten times so as to measure impalement resistance (N). Test 1 used samples having a diameter D of 0.43 mm. Test 2 used samples having a diameter D of 0.63 mm.

Results of Test 1 for the triangular needle A according to the present invention show an average of approximately 0.6N for the first impalement of the ten samples, and an average of approximately 0.8N for the tenth impalement. Moreover, there is little fluctuation of impalement resistance in the ten samples, within a range of 0.5N at most. In contrast, the conventional triangular needles show an average of approximately 1.2N for the first impalement, and an average of approximately 1.7N for the tenth impalement. Fluctuation was great, within a range of approximately 1N at most.

Accordingly, as a result of Test 1, it can be said that the triangular needle A according to the present invention is highly effective, having only approximately half of the impalement resistance of the conventional triangular needle and little fluctuation from sample to sample.

The results of Test 2 for the triangular needle A according to the present invention show an average of approximately 0.6N for the first impalement of the ten samples, and an average of approximately 1.1N for the tenth impalement. Moreover, there is little fluctuation of impalement resistance in the ten samples, within a range of 0.2N at most. In contrast, the conventional triangular needles show an average of approximately 1.6N for the first impalement, and an average of approximately 2.4N for the tenth impalement. There is much fluctuation, within a range of approximately 2N at most.

Accordingly, as a result of Test 2, it can be said that the triangular needle A according to the present invention is effective, having only approximately half of the impalement resistance of the conventional triangular needle and little fluctuation from sample to sample. This is because the increasing rate of thickness of the first cutting blade is lower than increasing rate of thickness of the second cutting blade since the length of the first cutting blade is set in accordance with the length of the second cutting blade, and as a result, reducing the resistance when incising tissue.

Specifically, since the angle α made by the edges 5 including the point 3 and the angle θ made by the second cutting blade 2 and the second bottom surface are set to approximately the same angle at the front end part of the conventional triangular needle, it is possible to endure ten impalement tests without crushing or bending even during the initial impalement.

INDUSTRIAL APPLICABILITY

The triangular needle A according to the present invention is applicable as either a straight suture needle or a curved suture needle.

EXPLANATION OF REFERENCES

A: Triangular needle
B: Base point
1: First cutting blade
2: Second cutting blade
3: Point
4, 5: Edge
10: Cutting blade part
11: First slanted surface
11a: Cut upper rim
12: Second slanted surface
13: First bottom surface
14: Second bottom surface
20: Ridge
20a: Ridge part
30: Body part
40: Base end part
41: End surface

The invention claimed is:

1. A medical suture needle having a triangular cross section made of austenitic stainless steel having a fibrously extending structure, comprising:
   two first slanted surfaces ground and sandwiching a ridge, and a first bottom surface sandwiched between the two first slanted surfaces and ground; and
   two second slanted surfaces ground and sandwiching the ridge on a front end side of the fist slanted surfaces, and a second bottom surface ground and sandwiched between the two second slanted surfaces, wherein
   the ridge is formed comprising a first cutting blade that is formed by the two first slanted surfaces intersecting, a ridge part that is formed on a body part side of the first cutting blade without the two first slanted surfaces intersecting, and a second cutting blade that is formed by the two second slanted surfaces ground, intersecting and sandwiching the first cutting blade on a front end side of the first cutting blade,
   the first bottom surface and the second bottom surface form a continuous surface, and are slanted so that they approach the first cutting blade and the second cutting blade,
   a length of the first cutting blade is within a range of 3 to 20 times a length of the second cutting blade,
   a point of the second cutting blade is positioned deviating from a longitudinal axis of the needle and inward toward the longitudinal axis of the needle from a circumferential surface of the needle, and
   wherein grind marks of the first slanted surfaces are formed along the length of the medical suture needle, and grind marks of the second slanted surfaces and the bottom surface are formed crossing the length of the medical suture needle.

2. The medical suture needle of claim 1, wherein an angle made by cut upper rims having as a starting point an end part of the first cutting blade on the two slanted surfaces that are ground and sandwiching the ridge is smaller than 20 degrees.

* * * * *